US010656141B2

(12) United States Patent
Conolly et al.

(10) Patent No.: US 10,656,141 B2
(45) Date of Patent: May 19, 2020

(54) SELECTION OF AGENTS MODULATING GASTROINTESTINAL PAIN

(71) Applicant: BIOGAIA AB, Stockholm (SE)

(72) Inventors: Eamonn Conolly, Lidingo (SE); Wolfgang Kunze, Hamilton (CA); John Bienenstock, Toronto (CA)

(73) Assignee: BIOGAIA AB, Stockholm (SE)

( * ) Notice: Subject to any disclaimer, the term of this patent is extended or adjusted under 35 U.S.C. 154(b) by 0 days.

(21) Appl. No.: 15/981,244

(22) Filed: May 16, 2018

(65) Prior Publication Data

US 2018/0259503 A1 Sep. 13, 2018

Related U.S. Application Data

(62) Division of application No. 15/111,930, filed as application No. PCT/SE2015/050064 on Jan. 23, 2015, now abandoned.

(30) Foreign Application Priority Data

Jan. 23, 2014 (SE) ...................................... 1450065
Jul. 1, 2014 (SE) ...................................... 1450813

(51) Int. Cl.
*G01N 33/50* (2006.01)
*G01N 33/68* (2006.01)
*A61K 35/74* (2015.01)
*A61K 35/00* (2006.01)
*A61K 45/06* (2006.01)

(52) U.S. Cl.
CPC ......... *G01N 33/5041* (2013.01); *A61K 35/74* (2013.01); *A61K 45/06* (2013.01); *G01N 33/6872* (2013.01); *G01N 33/6893* (2013.01); *A61K 2035/11* (2013.01); *G01N 2333/705* (2013.01); *G01N 2800/06* (2013.01)

(58) Field of Classification Search
CPC ........... G01N 33/5041; G01N 33/6872; G01N 33/6893; G01N 2333/705; G01N 2800/06; A61K 45/06; A61K 35/74
See application file for complete search history.

(56) References Cited

U.S. PATENT DOCUMENTS

2008/0051454 A1 2/2008 Wang

FOREIGN PATENT DOCUMENTS

| EP | 0861905 | 9/1998 |
| JP | 2012188409 | 10/2012 |
| KR | 20110027920 | 3/2011 |
| WO | 2006/110088 | 10/2006 |
| WO | 2007/142596 | 12/2007 |
| WO | 2008/090434 | 7/2008 |
| WO | 2009/155932 | 12/2009 |
| WO | 2013/141202 | 9/2013 |

OTHER PUBLICATIONS

Lin et al., J. Med. Chem. 2011, vol. 54, No. 11, p. 3746-3755.*
Reubish et al., BioTechniques, 2009, vol. 47, No. 3, p. iii-ix.*
Savino et al., Pediatrics, 2010, vol. 126, p. e526-e533.*
Holzer et al. "TRPV1 and the gut: from a tasty receptor for a painful vanilloid to a key player in hyperalgesia", European Journal of Pharmacology, Elsevier Science, NL, vol. 500, No. 1-3, Oct. 2004, 12 pages.
Holzer, Peter, "Transient receptor potential (TRP) channels as drug target for diseases of the digestive system", Pharmacology and Therapeutics, vol. 131, No. 1, 2011, 30 pages.
International Search Report, PCT Application No. PCT/SE2015/050064, dated Apr. 2, 2015, 4 pages.
Kamiya T et al. Inhibitory effects of Lactobacillus reuteri on visceral pain induced by colorectal distension in Sprague-Dawley rats. Gut. 2006; 55: 191-196.
Massi M et al. Effects of probiotic bacteria on gastrointestinal motility in guinea-pig isolated tissue. World J Gastroenterol. Oct. 7, 2006; 12(37): 5987-5994.
Peng et al. "The vanilloid receptor TRPV1: Role in cardiovascular and gastrointestinal protection", European Journal of Pharmacology, 627, (2010), 7 pages.
Ravnefjord A et al. Involvement of the transient receptor potential vanilloid 1 (TRPV1) in the development of acute visceral hyperalgesia during colorectal distention in rats. European Journal of Pharmacology. 2009; 611: 85-91.
Sophie A. Van Diest et al. "Relevance of mast cell nerve interactions in intestinal nociception", Biochimica et Biophysica Acta. Molecular Basis of Disease, Amsterdam, NL, vol. 1822, No. 1, Mar. 2011, 12 pages.
Written Opinion of the International Searching Authority, PCT Application No. PCT/SE2015/050064, dated Jul. 30, 2015, 6 pages.
X. Ma et al. "Lactobacillus reuteri ingestion prevents hyperexcitability of colonic DRG neurons induced by noxious stimuli", American Journal of Physiology: Gastrointestinal and Liver Physiology, vol. 296, No. 4, Apr. 2009, 10 pages.
Koplas P. A. et al., The Role of Calcium in the Desensitization of Capsaicin Responses in Rat Dorsal Root Ganglion Neurons. J. Neurosci, May 15, 1007, vol. 17, No. 10, pp. 3525-3537, Materials and Methods and Figures 1-3.
Romano C. et al., Lactobacillus reuteri in children with functional abdominal pain (FAP). J. Paediatr Child Health, Jul. 8, 2010, vol. 50, No. 10, pp. E68-E71.
Orel R., Effectiveness of Lactobacillus reuteri for prevention and treatment of functional gastrointestinal disorders in infants, children and adolescents (Review). Zdrav Vestn 2013; 82 Supl 1: 1-83-93.
Btesh J. et al., Mapping the Binding Site of TRPV1 on AKAP79: Implications for Inflammatory Hyperalgesia. J. Neurosci, May 22, 2013, vol. 33, No. 21, pp. 9184-9193.

* cited by examiner

Primary Examiner — Kade Ariani
(74) Attorney, Agent, or Firm — Myers Bigel, P.A.

(57) ABSTRACT

The present embodiments relate to selection of agents effective in reducing or preventing gastrointestinal pain in a subject. Such an agent is selected and identified if it is capable of reducing spontaneous and/or induced transient receptor potential vanilloid 1 (TRPV1) activation.

7 Claims, 9 Drawing Sheets

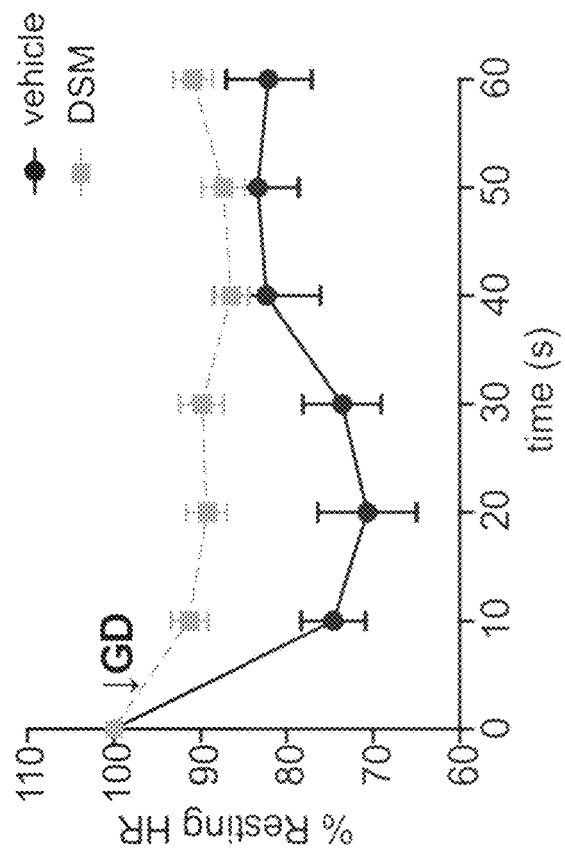
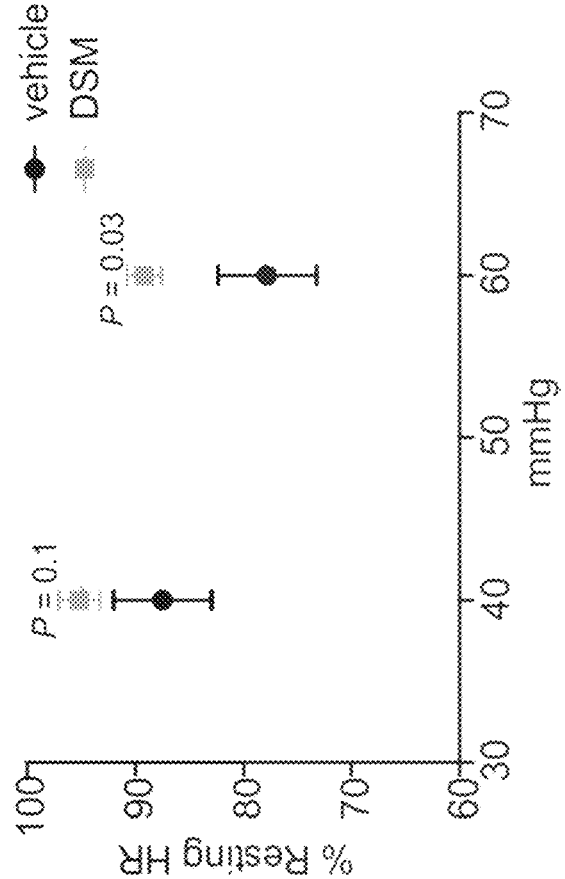
Fig. 6A
Fig. 6B

SELECTION OF AGENTS MODULATING GASTROINTESTINAL PAIN

STATEMENT OF PRIORITY

This application is a divisional application of U.S. patent application Ser. No. 15/111,930, which is a 35 U.S.C. § 371 national phase application of International Application Serial No. PCT/SE2015/050064, filed Jan. 23, 2015, which claims the benefit, under 35 U.S.C. § 119 (a) of Swedish Patent Application No. 1450065-6, filed Jan. 23, 2014, and Swedish Patent Application No. 1450813-9, filed Jul. 1, 2014, the entire contents of each of which are incorporated by reference herein.

TECHNICAL FIELD

The present invention relates primarily to modulation of gastrointestinal pain and in particular to selection of agents, such as Lactic Acid bacteria, capable of modulating gastrointestinal pain and the use of such agents.

BACKGROUND

Gastrointestinal pain is a symptom of many conditions, diseases and disorders associated with the gastrointestinal tract. Functional abdominal pain, refers to recurrent abdominal pain. The vast majority of patients with recurrent abdominal pain have "functional" or "non-organic" pain, meaning that the pain is not caused by physical abnormalities. Various motility disorders are also associated with pain and constipation or diarrhea. The term is used to describe a variety of disorders in which the gut has not developed properly or lost its ability to coordinate muscular activity due to various causes.

Such disorders may manifest in a variety of ways, and includes but are not limited to the following:

Abdominal distention
Recurrent obstruction
Abdominal colicky pain
Constipation
Gastroesophageal reflux disease
Intractable, recurrent vomiting
Diarrhea
Irritable bowel syndrome (IBS)
Inflammatory bowel disease
Fecal incontinence
Infantile colic
Frequent recurrent abdominal pain (FRAP)
Regurgitation
Food intolerance In a broad sense, any significant alteration in the transit of foods and secretions into the digestive tract may be considered an intestinal motility disorder and this is type of disorder is often associated with gastrointestinal pain.

Proper coordinated movements of the stomach and intestines are required to digest and propel intestinal contents along the digestive tract. The patterns of contraction and relaxation necessary for proper motility of the gastrointestinal (GI) tract are complex and use the nerves and muscles within the GI walls. Every day, at any time, many factors can influence GI motility, e.g. physical exercise and emotional distress. Newborn infants have to develop the complex system of motility in the GI tract. Dysfunctional gastrointestinal motility is often associated with GI pain.

Aging, dementia, stroke, Parkinson disease, spinal cord injuries, rectal tears during birthing, diabetes, surgical complications and neuromuscular disorders, e.g. myasthenia gravis, may cause motility disorders that are associated with pain.

Irritable bowel syndrome (IBS), a commonly diagnosed disorder of intestinal motility and GI pain, has been considered a disease of the colon for decades, but research on GI motility has demonstrated that underlying motility disturbances can occur also in the small bowel. IBS can often be accompanied by GI pain and TRPV1 immunoreactivity has been shown to be markedly increased in IBS patients (Akbar, Yiangou et al, Gut 2008).

Constipation, often associated with GI pain, is the most common digestive complaint in the United States but despite its frequency, often remains unrecognized until the patient develops secondary disorders, such as anorectal disorders or diverticular disease. As mentioned previously, GI pain is a common symptom of constipation.

Constipation is quite common during pregnancy. The muscle contractions that normally move food through the intestines slow down because of higher levels of the hormone progesterone and possibly extra iron taken as prenatal vitamin. This is often also accompanied by lower abdominal pain.

Constipation is also associated with increased age and the so called "the aging gut" commonly found especially in people over 70 and in chronic care institutions.

At the other end of the aging spectrum intestinal motility disorders, persistent or excessive crying from infant colic is one of the most distressing problems of infancy. It is distressing for the infant, the parents, and the involved healthcare professionals. Colic pain often starts and stops abruptly Intestinal hypermotility secondary to a presumed autonomic imbalance also has been proposed as one etiology for colic. Many of the mechanisms that regulate motor activity are immature in infants. The immaturity of these mechanisms may result in increased vulnerability to feeding intolerance. Thus, colic may be a common clinical manifestation in the subpopulation of infants who have maturational dysfunction in one or more of the aspects of motility regulation and often leading to GI pain for the infant.

Intestinal motility disorders applies to abnormal intestinal contractions often associated with GI pain, there are many different kinds of treatments and recommendations for the different disorders, some which work better than many others.

So there is an overall need and specific problems to solve for various motility disorders and pain disorders namely; How to best select agents to prevent or reduce gastrointestinal pain?

Transient receptor potential vanilloid 1 (TRPV1) is a $Ca^{2+}$ permeant cation channel expressed in e.g. the peripheral nervous system (PNS), the central nervous system (CNS), the respiratory system and the gastrointestinal tract. TRPV1 is activated by physical and chemical stimuli, e.g. temperature, pH change and capsaicin, and is critical for the detection of nociceptive and thermal inflammatory pain. In the gastrointestinal tract, TRPV1 immunoreactivity can e.g. be found in visceral sensory afferents and TRPV1 cells transmit e.g. gastric pain sensation to the higher centers of the brain. TRPV1 is thought to be involved in several gastrointestinal conditions that are associated with pain sensations and TRPV1 immunoreactivity has been shown to be markedly increased in e.g. IBS (Akbar, Yiangou et al, Gut 2008). As an example of this, patients diagnosed with active inflammatory bowel disease demonstrate a greatly increased TRPV1 immunoreactivity in colonic nerve fibers (Wang, Miyares and Ahern, 2005 J. Physiol.).

Although TRPV1 is considered to be a potential target for developing drugs to treat different modalities of pain, the widespread expression of the receptor may result in adverse events limiting the use of systemic TRPV1 antagonists in treating gastrointestinal pain. In particular, antagonizing the receptor could potentially lead to cardiovascular complications as a result of decreased vasoactive peptide release.

SUMMARY OF THE INVENTION

It is a general objective to find agents suitable for reducing or preventing gastrointestinal pain.

It is a particular objective to provide a method for selecting agents, preferably bacterial strains and more preferably Lactic Acid Bacteria, effective in reducing or preventing gastrointestinal pain.

These and other objectives are met by embodiments as disclosed herein.

An aspect of the embodiments relates to a method for selecting an agent effective in reducing or preventing gastrointestinal pain in a subject. The method comprises selecting an agent capable of reducing spontaneous and/or induced transient receptor potential vanilloid 1 (TRPV1) activation.

Another aspect of the embodiments relates to an agent selected by the above identified method.

A further aspect of the embodiments relates to an agent obtainable by the above identified selection method for use in reducing or preventing gastrointestinal pain in a subject.

Yet another aspect of the embodiments relates to a composition comprising an agent obtainable by the above identified selection method and at least one additional component selected from a group consisting of a pharmaceutically acceptable carrier, a pharmaceutically acceptable diluent, a pharmaceutically acceptable excipient, a foodstuff, a food supplement and another preventive or therapeutic agent.

A related aspect of the embodiments defines an agent as defined above or a composition as defined above for use in reducing or preventing gastrointestinal pain in a subject.

Another related aspect of the embodiments defines use of an agent obtainable by the above identified selection method or as defined above or a composition as defined above for the manufacture of a medicament, a food product or a food supplement product for reducing or preventing gastrointestinal pain in a subject.

Yet another aspect of the embodiments relates to a method of reducing or preventing gastrointestinal pain in a subject. The method comprises administering an effective amount of an agent obtainable by the above identified selection method or as defined above or a composition as defined above to the subject.

The present embodiments provide an efficient technology that can be used to select or identify agents, in particular bacterial strains, such as Lactic Acid bacteria, that can be used to reduce or prevent gastrointestinal pain in subjects, preferably human subjects, suffering from a disorder or disease causing or is associated with gastrointestinal pain.

BRIEF DESCRIPTION OF THE FIGURES

The embodiments, together with further objects and advantages thereof, may best be understood by making reference to the following description taken together with the accompanying figures, in which:

FIGS. 6A-6B show that 9 day feeding with DSM 17938 reduced gastric distension evoked bradycardia. A) Summary values for percent decreases in resting heart rate evoked by 40 and 60 mmHg gastric distension (P values, unpaired t tests). B) Summary plots showing how resting heart rate changed over time in response to 60 mmHg gastric distension. (P=0.01, two-way ANOVA test).

DETAILED DESCRIPTION

Figure 1B:
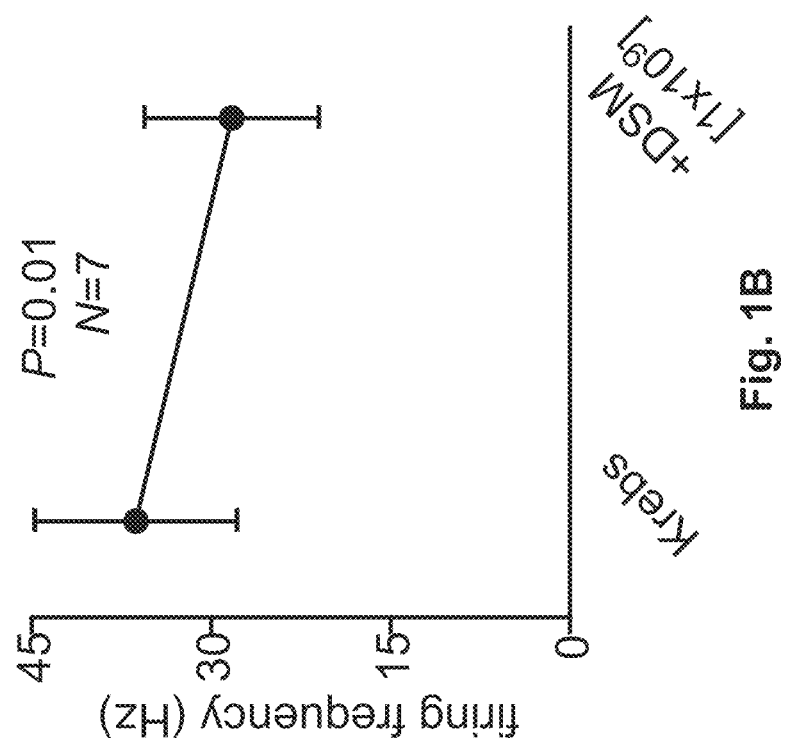
FIGS. 1A-1E show mesenteric multiunit spontaneous firing after addition of $1\times10^8$ DSM 17938 units (cfu)/ml. (A), $1\times10^9$ cfu/ml DSM 17938 (B), diluted DSM 17938 conditioned medium (1:5) (C), $1\times10^9$ cfu/ml γ-irradiated DSM 17938 (D), and diluted medium alone (1:5) (E) (Wilcoxon tests).

To facilitate understanding of the invention, a number of terms are defined below.

"Gastrointestinal pain", also referred to as GI pain, denotes pain in the gastrointestinal system of a subject. Such gastrointestinal pain is often caused by or is associated with, i.e. is a symptom of or an ailment component of, various diseases and disorders, typically of the gastrointestinal system. Gastrointestinal pain includes general pain in the gastrointestinal system, often denoted general gastrointestinal pain in the art, pain associated with intestinal motility disorders, pain from inflammatory bowel diseases and irritable bowel syndrome, gastric pain, general abdominal pain, visceral pain, functional abdominal pain, frequent recurrent abdominal pain and pain in other functional gastrointestinal disorders.

"Functional abdominal pain" refers to recurrent abdominal pain. The vast majority of patients with recurrent abdominal pain have "functional" or "non-organic" pain, meaning that the pain is not caused by physical abnormalities.

"Intestinal motility disorders" is used to describe a variety of disorders in which the gut has not developed properly or lost its ability to coordinate muscular activity due to various causes. Such disorders may manifest in a variety of ways, and includes but are not limited to the following:

Abdominal distention
Recurrent obstruction
Abdominal colicky pain
Constipation
Gastroesophageal reflux disease
Intractable, recurrent vomiting
Diarrhea
Irritable bowel syndrome (IBS)
Inflammatory bowel disease
Fecal incontinence
Infantile colic
Frequent recurrent abdominal pain (FRAP)
Regurgitation
Food intolerance In a broad sense, any significant alteration in the transit of foods and secretions into the digestive tract may be considered an intestinal motility disorder and this is often associated with gastrointestinal pain.

"Gastric pain" is a collective term used to describe pain or discomfort in the upper abdomen.

In an embodiment, the cause of the gastric pain is selected from the group comprising, such as consisting of, non-ulcer dyspepsia, peptic ulcer, gastroesophageal reflux disease and gastritis.

In a particular embodiment, the cause of the gastric pain is non-ulcer dyspepsia and/or gastritis.

As used herein the term "firing frequency" is used to measure the sensory spike trains to the brain.

As used herein the term "intraluminal peak pressure" (PPr) is based on intraluminal pressure recordings, where intraluminal pressure changes are measured at the midpoint of the longitudinal axis of the gut segment. The pressure signal is analyzed and intraluminal peak pressure (PPr) is identified and measured.

As used herein the term "migrating motor complex frequency" (MMC frequency) is calculated by counting the number of dark MC bands in spatiotemporal maps.

As used herein the term "migrating motor complex velocity" (MMC velocity) is measured from the slope(s) of each band in the spatiotemporal map generated by migrating motor complexes.

As used herein the term "agent" is used to mean any substance or material including whole cells; microorganisms; conditioned medium; proteins, peptides, enzymes, and/or molecules derived from such a conditioned medium; proteins, peptides, enzymes and/or molecules secreted or derived from whole cells or microorganisms; or other biological or chemical material that can be used to modulate gastrointestinal pain in the gastrointestinal system of a mammal. An example of preferred agents are bacterial strains, e.g. probiotic bacterial strains, and in particular Lactic Acid bacterial strains. Another example of preferred agent is a conditioned medium from bacterial strains, e.g. probiotic bacterial strains, and in particular Lactic Acid bacterial strains.

A conditioned medium, sometimes also referred to as conditioned culture medium, is a (culture) medium in which cells have been cultured for a period of time. The cells cultured in the medium "condition" the medium by releasing or secreting various components or molecules, such as proteins, peptides, enzymes, cytokines, chemokines, chemicals, etc.

It is beginning to be accepted that intestinal microorganisms signal to the brain as part of the so called microbiome-gut-brain axis. However, very little is known about the role of the gut microbiome in the development or function of the nervous system. Presently only little is known about the quantitative nature of the nervous signal relayed from gut to the central nervous system.

Single sensory neurons, including those among the vagus fibers, represent continuous physical stimuli as patterned spike trains that encode the nature and intensity of the stimulus. In addition to this, stimuli may be represented in a population code determined by the number of active fibres in the bundle. All the information reaching the brain via primary afferents has to be encoded in the language of neuronal spike trains. Therefore, knowing how the sensory spike trains are affected by various agents, such as commensals, probiotic strains and different substances, enable us to identify new beneficial gut microorganisms and their active molecules by their effects on primary afferent firing as well as new drugs and other compounds that in various fashion can intervene in this signaling system, particularly by modulating TRPV1 activation.

The method of the embodiments herein is employed for selecting an agent for use in reduction or prevention of gastrointestinal pain by inhibiting signaling through the TRPV1 receptor. The method of the embodiments can thereby be used for evaluating agents that potentially could be effective in preventing gastrointestinal pain and/or effective in reducing, inhibiting or treating gastrointestinal pain. Thus, the method can be used to identify effective agents capable of modulating gastrointestinal pain associated with the peripheral (enteric) and/or the central nervous system.

Thus, an aspect of the embodiments relates to a method for selecting an agent effective in, i.e. for use in, reducing or preventing gastrointestinal pain in a subject. The method comprises selecting an agent capable of reducing spontaneous and/or induced transient receptor potential vanilloid 1 (TRPV1) activation.

The embodiments are thereby based on using the TRPV1 signaling pathway as a selection tool in identifying agents that are effective in modulating, in particular preventing or reducing, such as inhibiting or treating, gastrointestinal pain in subjects suffering from diseases or disorders involving or causing such gastrointestinal pain and which could be denoted gastrointestinal pain diseases or disorders.

The method of the embodiments is typically performed in vitro or ex vivo as is further disclosed herein. However, the agent is preferably capable of reducing spontaneous and/or induced TRPV1 activation in the subject when administered to the subject.

The method of the embodiments may, thus, be used to find suitable agents for reducing or preventing gastrointestinal pain in different gastrointestinal pain disorders and diseases. Agents are chosen to affect the TRPV1 activation of the subject in a beneficial way in order to modulate, i.e. preferably prevent, reduce or treat the gastrointestinal pain.

In an embodiment, the disorder or disease associated with gastrointestinal pain to be prevented or treated with an agent selected by the method is a gastrointestinal pain disorder or disease.

In an embodiment, the gastrointestinal pain is gastric pain.

In an embodiment, the gastrointestinal pain is visceral pain.

In an embodiment, the gastrointestinal pain may be present in a subject suffering from colic.

In an embodiment, the gastrointestinal pain may be present in a subject suffering from irritable bowel syndrome (IBS).

In an embodiment, the gastrointestinal pain may be present in a subject suffering from constipation. Gastrointestinal pain may be present in subjects suffering from intestinal motility disorders as defined in the foregoing.

Thus, in an embodiment the subject is suffering from an intestinal motility disorder with associated gastrointestinal pain.

The method of the embodiments is based on the unexpected discovery that gastrointestinal pain including pain associated with different conditions and disorders such as motility disorders, and manifested centrally or peripherally, is connected to TRPV1 activation, which can be modulated by previously unknown agents, such as Lactic Acid bacteria.

One kind of gastrointestinal pain is visceral pain that results from the activation of nociceptors of the abdominal viscera (organs). Visceral structures are highly sensitive to distension (stretch), ischemia and inflammation, but relatively insensitive to other stimuli that normally evoke pain. Visceral pain is diffuse, difficult to localize and often referred to a distant, usually superficial, structure. It may be accompanied by symptoms such as nausea, vomiting, changes in vital signs as well as emotional manifestations. The pain may be described as sickening, deep, squeezing, and dull. Distinct structural lesions or biochemical abnormalities explain this type of pain in only a proportion of patients. These diseases are sometimes grouped under gastrointestinal neuromuscular diseases (GINMD). Persons can also experience visceral pains, often very intense in nature, without any evidence of structural, biochemical or histolopathologic reason for such symptoms.

A nociceptor is a sensory receptor that responds to potentially damaging stimuli by sending action potentials to specific nociceptive neurons (Aδ or C) which transmit to the anterolateral tracts of the spinal cord (plus a minor vagal projection) and then to the thalamus, and prosencephalon including the insular and cingulate cortices. Critical for pain perception originating in the gut pathology is the activation of pain messages from the gut to the central nervous system via extrinsic primary afferent fibers that travel in mesenteric afferent nerve bundles.

The method can be used to screen agents in order to select agents with desired properties, e.g. reduction in TRPV1 activation, for use in reducing or preventing gastrointestinal pain. The parameter to be measured in the method, i.e. spontaneous and/or induced TRPV1 activation, can be monitored and determined in different models and systems. Using this information, a profile can be obtained useful for defining the detailed and potentially nuanced effects that specific agents have on pain signaling in gastrointestinal pain.

Other parameters that can be measured in the method include general pain signaling, nerve firing activity, e.g. mesenteric nerve bundle analysis, and possibly using different in vivo models of gastrointestinal pain.

In an embodiment, TRPV1 activation is measured in cells expressing TRPV1, such as dorsal root ganglion (DRG) neurons, CaCo2 cells or another standard human intestinal epithelial cell line. Both spontaneous TRPV1 activation and TRPV1 activation after induction by e.g. capsaicin, pH change or temperature can be measured. Generally, any cell or tissue which expresses TRPV1 can be used to measure TRPV1 activation according to the embodiments.

Thus, in an embodiment the method comprises contacting a cell expressing TRPV1 with an agent to be tested. The method also comprises measuring spontaneous and/or induced TRPV1 activation in the cell following, i.e. after, contacting the cell with the agent to be tested. The method further comprises comparing the measured spontaneous and/or induced TRPV1 activation with a control TRPV1 activation. In this embodiment, the method further comprises selecting the agent to be tested as an agent effective in reducing or preventing gastrointestinal pain if the measured spontaneous and/or induced TRPV1 activation is lower than the control TRPV1 activation.

The control TPRV1 activation can be determined according to various embodiments. For instance, the TRPV1 activation could be predefined and determined from TRPV1 expressing cells with an activation level that represents normal or baseline activation corresponding to e.g. substantially no gastrointestinal pain.

However, a preferred embodiment of determining the control TRPV1 activation is to use the TRPV1 expressing cell as an internal control. Hence, in an embodiment the method comprises measuring spontaneous and/or induced TRPV1 activation in the cell prior to contacting the cell with the agent to be tested. The method also comprises determining the control TRPV1 activation based on the spontaneous and/or induced TRPV1 activation measured in the cell prior to contacting the cell with the agent to be tested.

In this approach, spontaneous and/or induced TRPV1 activation measurements are therefore preferably performed twice: prior to contacting the cell with the agent to be tested and following contacting the cell with the agent to be tested.

Alternatively, the spontaneous and/or induced TRPV1 activation measurements could be performed in two parallel experiments: one experiment where a cell is contacted with the agent to be tested and one control experiment where a cell is not contacted with the agent. The cells used in the two experiments are then of the same type, such as both DRG neurons, CaCo2 cells or another standard human intestinal epithelial cell line. The spontaneous and/or induced TRPV1 activation is measured in both experiments and then compared to each other.

The cell to be used in the method can be any cell expressing TRPV1 including, but not limited, to ex vivo preparations, cell lines expressing TRPV1, such as human intestinal epithelial cell lines expressing TRPV1, and primary cells expressing TRPV1.

The measured spontaneous and/or induced TRPV1 activation and the control TRPV1 activation can generally be expressed as a respective parameter value or metric, including a value representing spontaneous and/or induced TRPV1 activation level.

In an embodiment, primary cells such as e.g. dorsal root ganglion (DRG) neurons are used for analyzing TRPV1 activation.

In another embodiment, cell lines expressing TRPV1 such as CaCo2 or another standard human intestinal epithelial cell line are used for analyzing TRPV1 activation.

In other embodiments, commercially available cell lines expressing TRPV1 are used for analyzing TRPV1 activation, see e.g. cat: no CT6105 from Chantest.

It is also possible to user reporter gene cells, also denoted reporter cells in the art, that can be used to monitor and measure TRPV1 expression and/or spontaneous and/or induced TRPV1 activation.

Several different methods can be used to study TRPV1 activation, including but not limited to functional analysis using e.g. calcium influx induced by e.g. capsaicin and/or its prevention by an agent in cells expressing TRPV1 and firing frequencies of mesenteric nerve bundles, spontaneous and/or induced by e.g. capsaicin. In another embodiment, functional assessment of temperature-gated ion-channel activity using a real-time PCR machine, as described in Reubish, Emerling et al., BioTechniques 2009, can be used to analyze TRPV1 activation. In another embodiment, reporter mice for the TRPV1 channel can be used to investigate TRPV1 activation. Various in vivo paradigms can also be used to analyze effects on pain in the invention. These methods include e.g. gastric distention and effects on heart rate (see Example 3) and colorectal distension models.

Hence, in an embodiment, the method comprises measuring $Ca^{2+}$ influx in the cell induced by capsaicin or another substance capable of inducing TRPV1 activation, e.g. a capsaicin analogue or other substances capable of activating TRPV1. Also exposing the cell to selected physical conditions can be used to induce TRPV1 activation, including changing pH or temperature. Thus, exposing the cell to acidic pH, basic pH and/or heat (elevated temperatures, typically above about 42° C.) can induce TRPV1 activation. In this embodiment, the $Ca^{2+}$ influx in the cell expressing TRPV1 is thereby used as a parameter representing TRPV1 activation. A reduction in TRPV1 activation, and in particular a reduction in pH-induced, heat-induced and/or capsaicin-induced TRPV1 activation, can then be measured as a reduction in $Ca^{2+}$ influx. In another embodiment, the method comprises measuring temperature-gated ion-channel activity in the cell. In this embodiment, the temperature-gated ion-channel activity in the cell expressing TRPV1 is used as a parameter representing TRPV1 activation. The temperature-gated ion-channel activity could be spontaneous or induced, such as induced by increased temperature. A reduction in TRPV1 activation can then be measured as a reduction in temperature-gated ion-channel activity in the cell.

In an embodiment, TRPV1 activation is measured using mesenteric afferent nerve bundle experiments. Thus, another parameter that can be measured is the spontaneous and/or induced, e.g. by capsaicin, pH change or heat, firing frequencies of mesenteric afferent nerve bundles. This technique can be used to determine changes in the excitability of the mesenteric nerve fibers induced by different agents to be tested. In an embodiment, a gastrointestinal segment is excised with or without the mesenteric arcade containing the nerve bundle supplying the segment made up of both spinal and vagal fibers for nerve bundle recordings ex vivo (see Example 1).

In some embodiments, the regional specificity of the gastrointestinal tract is of importance. Appropriate segments for mesenteric nerve analysis of the method preferably comprises an appropriate nerve bundle to enable the measurement of mesenteric afferent nerve firing. This can conveniently be provided by having a gastrointestinal segment with attached mesenteric tissue (see Example 1). Thus, this embodiment is conveniently carried out on ex vivo segments from an appropriate experimental animal, for example on mouse gastrointestinal segments (e.g. mouse colon or jejunum segments). The ability to carry out a comparison of the effect of an agent on the small versus the large intestine could be advantageous, particularly as, depending on the intestinal motility disorder to be treated and the clinical stage and symptoms thereof, a treatment which is region-specific, e.g. specific for either the small or large intestine might be beneficial.

In an embodiment afferent mesenteric nerve spinal traffic is analyzed for specific and selected parts of the gut. It has been surprising to find that different agents, such as Lactic Acid bacteria, can influence or modulate gastrointestinal pain signaling systems in one part, but not in another part of the GI-tract, and via different nerve pathways such as vagal or for visceral pain through the dorsal root ganglion.

Thus, in an embodiment the method comprises contacting an ex vivo gastrointestinal segment with attached mesenteric tissue with an agent to be tested. The method also comprises measuring spontaneous and/or induced mesenteric afferent firing in the ex vivo gastrointestinal segment following contacting the ex vivo gastrointestinal segment with the agent to be tested. The method further comprises comparing the spontaneous and/or induced measured mesenteric afferent firing with a control mesenteric afferent firing. In this embodiment, the method further comprises selecting the agent to be tested as an agent effective in reducing or preventing gastrointestinal pain if the measured spontaneous and/or induced mesenteric affenerent firing is lower than the control mesenteric afferent firing.

The control mesenteric afferent firing can be determined as discussed in the foregoing using the ex vivo gastrointestinal segment as an internal control. In such a case, the method comprises measuring spontaneous and/or induced mesenteric afferent firing in the ex vivo gastrointestinal segment prior contacting the ex vivo gastrointestinal segment with the agent to be tested. The method also comprises determining the control mesenteric afferent firing based on the spontaneous and/or induced mesenteric afferent firing measured in the ex vivo gastrointestinal segment prior contacting the ex vivo gastrointestinal segment with the agent to be tested.

Alternatively, two parallel experiments can be conducted. In one of them an ex vivo gastrointestinal segment is contacted with the agent to be tested and in the other one, control experiment, an ex vivo gastrointestinal segment is not contacted with the agent. The spontaneous and/or induced mesenteric afferent firing is measured in both experiments and compared to each other.

Analyzing one or more of these parameters above will result in a method of selecting agents effective in reducing or preventing gastrointestinal pain.

In a particular embodiment, the ex vivo gastrointestinal segment is selected from an ex vivo colon or jejunum segment. In such a case, the method comprises contacting an ex vivo colon or jejunum segment with attached mesenteric tissue with the agent to be tested.

Examples of appropriate methods and apparatus for analyzing spontaneous and/or induced TRPV1 activation are described in the Examples and Figures.

Thus, in preferred methods, the analysis presented will give data on spontaneous and/or induced TRPV1 activation. Analyzing one or several of these parameters will result in a preferred method of selecting agents effective in reducing and/or preventing gastrointestinal pain.

The method of the embodiments can, thus, be used to find agents suitable for treatment, prevention and/or reduction of gastrointestinal pain, by using the model herein.

The method presented will provide data on spontaneous and/or induced TRPV1 activation using different models. Analyzing this parameter will result in a method of selecting for agents effective in reducing or preventing gastrointestinal pain.

In an embodiment, the method analyses the effect of an agent on TRPV1 activation (spontaneous and/or induced by e.g. capsaicin, pH change and/or heat and its prevention by an agent) and can thus be used as a read out for gastrointestinal pain signalling, i.e. whether or not an agent is likely to have an effect on gastrointestinal pain, e.g. visceral pain. An increase or no significant effect in spontaneous or induced (e.g. by capsaicin, pH change and/or heat) TRPV1 activity is indicative of an agent which is likely to result in an increase in gastrointestinal pain, or no significant effect on gastrointestinal pain, respectively, whereas a decrease in spontaneous and/or induced (e.g. by capsaicin, pH change and/or heat) TRPV1 activity is indicative of an agent which will reduce gastrointestinal pain. Preferred agents are thus those that result in a decrease in spontaneous and/or induced (e.g. by capsaicin) TRPV1 activity.

In another embodiment the method analyses the effect of an agent on TRPV1 activity by analyzing spontaneous and/or induced (e.g. by capsaicin, pH change and/or heat) mesenteric afferent nerve firing (pain signaling) and can thus be used as a read out for gastrointestinal pain, i.e. whether or not an agent is likely to have an effect on gastrointestinal pain, e.g. visceral pain. An increase or no significant effect on afferent nerve firing is indicative of an agent which is likely to result in an increase in gastrointestinal pain, or no significant effect on gastrointestinal pain, respectively, whereas a decrease in afferent nerve firing is indicative of an agent which will reduce gastrointestinal pain. Preferred agents are thus those that result in a decrease in afferent nerve firing, e.g. a decrease in the spontaneous and/or induced firing frequency of afferent nerve bundles.

The agent to be tested is added to the chosen system for TRPV1 activity analysis in any appropriate manner. In order to analyse the effect of the agent on pain signalling, the methods are conveniently carried out in the presence and the absence of the agent. For example, the method step is carried out before and after the agent is applied. Thus, in such methods the effect of the agent is compared to an appropriate control, for example the results in the presence of the test agent are compared with the results in the absence of a test agent, e.g. results with buffer alone as opposed to buffer plus agent.

The inventors have surprisingly found that certain strains of Lactic Acid Bacteria, e.g. DSM 17938, can reduce TRPV1 activation in different ex vivo and in vitro models (see Example 1 and 2). Hence, in a preferred embodiment the agent is a bacterial strain, more preferably a Lactic Acid bacteria. Thus, the method of the embodiments can advantageously be used to test various Lactic Acid bacteria in order to identify and select one or more Lactic Acid bacterial strains that are effective in reducing or preventing gastrointestinal pain in a subject as determined by the method in terms of being able to reduce spontaneous and/or induced TRPV1 activation.

Another aspect of the embodiments is an agent selected by the method of the embodiments, i.e. obtainable by the selection method.

A preferred agent is a microorganism, more preferably a bacterial strain, preferably a Lactic Acid bacteria, including parts or metabolites thereof.

Another preferred agent is a conditioned medium from such a microorganism.

A related aspect of the embodiments defines an agent obtainable by the selection method of the embodiments for use in reducing or preventing gastrointestinal pain in a subject.

In a particular embodiment, the agent is obtainable by the selection method of the embodiments to be capable of reducing spontaneous and/or induced RPTV1 activation for use in reducing or preventing gastrointestinal pain in a subject.

In an embodiment, for the reduction or prevention of gastrointestinal pain an agent will be selected which preferably acts to decrease pain signalling as assessed by monitoring the effect of the agent on spontaneous and/or induced TRPV1 activation. Such an agent will preferably act to reduce or decrease TRPV1 activation in DRG neurons, or other TRPV1-expressing cells or tissue. Preferably the agent will act to reduce the spontaneous and/or induced (e.g. by capsaicin, pH change and/or heat) TRPV1 activity using different in vitro systems or models including but not limited to primary cells and cell lines expressing the TRPV1 receptor as previously discussed.

In an embodiment, an agent will be selected which preferably acts to reduce or decrease TRPV1 activation in mesenteric afferent nerve bundles. The agent will act to reduce the spontaneous and/or induced (e.g. by capsaicin, pH change and/or heat) firing frequencies of mesenteric afferent nerve bundles.

It is clear from the above that the method of the embodiments can also be used to select or identify agents which are not appropriate for the treatment of gastrointestinal pain, for example agents that do not have a beneficial effect on reducing pain signalling. In particular those agents which show no effect on this parameter are unlikely to be suitable for the reduction or prevention of gastrointestinal pain. In addition, those agents which have an effect of increasing pain signalling as measured by an increase in spontaneous and/or induced TRPV1 activity are unlikely to be suitable for the reduction or prevention of gastrointestinal pain.

A further aspect of the embodiments relates to a composition comprising an agent selected by the method of the embodiments and at least one additional component. Thus at least one additional component is preferably selected from a group consisting of a pharmaceutically acceptable carrier, a pharmaceutically acceptable diluent, a pharmaceutically acceptable excipient, a foodstuff, a food supplement and another preventive or therapeutic agent.

Thus, an embodiment relates to a composition comprising an agent obtainable by the selection method of the embodiments and at least one additional component selected from a group consisting of a pharmaceutically acceptable carrier, a pharmaceutically acceptable diluent, a pharmaceutically acceptable excipient, a foodstuff, a food supplement and another preventive or therapeutic agent for use in reducing or preventing gastrointestinal pain in a subject.

The at least one additional component can be administered together with the agent selected according to the embodiments or can be administered separately. In addition, the at least one additional component can be administered at the same time as the agent selected according to the embodiments or at different time points. Suitable administration regimes and timings can readily be determined by the skilled person depending on the additional component in question.

In an embodiment, the at least one additional component is any appropriate nutritional component, e.g. a foodstuff or a food supplement.

In an embodiment, the another preventive or therapeutic agent can be any further agent, which is useful in the prevention or reduction, such as treatment, of the gastrointestinal pain in question.

In another embodiment, the another preventive or therapeutic agent is an agent capable of affecting gastrointestinal motility and/or mixing. The another preventive or therapeutic agent is then preferably capable of modulating (increasing or reducing, depending on the condition to be treated as is known in the art and described below) gastrointestinal motility and/or mixing.

In a further embodiment, the agent of the embodiments may have dual functions, i.e. have function on both gastrointestinal pain and gastrointestinal motility and/or mixing.

The agent selected according to present embodiments with the purpose of being effective in reducing or preventing gastrointestinal pain may also be subject to another or additional analysis or selection method with the purpose of determining whether the agent is additionally effective in modulating gastrointestinal motility and/or mixing. Such an agent may be interesting to use for prevention or treatment of e.g. motility disorders since it addresses both the gastrointestinal pain and the motility alteration in conjunction. Ways of analyzing motility and/or mixing are known in the art. Parameters to be analyzed include, but are not limited to, MMC frequency, MMC velocity, intraluminal pressure such as PPr and other functional models.

In motility analyses, changes in gastrointestinal motility induced by an agent can e.g. be detected as an alteration in motility pattern or contraction amplitudes. Some agents will have no effect at all. An agent which can increase gastrointestinal motility, for example by increasing the MMC frequency and/or MMC velocity and/or intraluminal pressure such as PPr will likely be useful to treat disorders associated with gastrointestinal pain in which it would be advantageous to increase the propulsive motility along the digestive tube such as constipation and colic.

Alternatively, if for example, the intestinal motility disorder for treatment is one in which it is desired to increase the transit time of material through the intestine, e.g. disorders involving rapid passage transit, such as IBS or diarrhea, then an agent of interest will in addition to its effects on gastrointestinal pain modulation act to decrease gastrointestinal motility, for example by decreasing MMC frequency or MMC velocity or intraluminal pressure, e.g. PPr. Preferred agents will decrease at least MMC velocity. Preferred agents will decrease two or more of these parameters, for example will decrease MMC velocity and MMC frequency or will decrease MMC frequency and intraluminal pressure (e.g. PPr) or will decrease MMC velocity and intraluminal pressure (e.g. PPr). Most preferred agents will decrease all of these parameters, for example will decrease MMC frequency, MMC velocity and intraluminal pressure (e.g. PPr). The motility analysis can be assessed on an appropriate gastrointestinal segment from the small or large intestine, for example a jejunal segment for the small intestine or a colon segment for the large intestine. In some embodiments, the use of large intestine, e.g. colon, segments is preferred.

A further aspect of the embodiments relates to an agent selected by the method of the embodiments or a composition as defined above for use in reducing or preventing gastrointestinal pain in a subject.

A related aspect of the embodiments defines use of an agent selected by the method of the embodiments, e.g. obtainable by the selection method according to the embodiments, or a composition as defined above for the manufacture of a medicament, a food product or a food supplement product for reducing or preventing gastrointestinal pain in a subject.

Another related aspect of the embodiments defines a method of reducing or preventing gastrointestinal pain in a subject. The method comprises administering an effective amount of an agent selected by the method of the embodiments, e.g. obtainable by the selection method according to the embodiments, or a composition as defined above to the subject.

In an embodiment of these aspects, the agent is a bacterial strain, preferably a Lactic Acid bacterial strain and more preferably a *Lactobacillus reuteri* strain, such as a bacterial strain capable of reducing spontaneous and/or induced TRPV1 activation, preferably a Lactic Acid bacterial strain capable of reducing spontaneous and/or induced TRPV1 activation and more preferably a *Lactobacillus reuteri* strain capable of reducing spontaneous and/or induced TRPV1 activation.

In an embodiment of these aspects, the agent is preferably *Lactobacillus reuteri* DSM 17938. In other embodiment, the agent is another Lactic Acid bacterial strain, i.e. the agent is a Lactic Acid bacterial strain other than *Lactobacillus reuteri* DSM 17938, preferably a *Lactobacillus reuteri* strain other than *Lactobacillus reuteri* DSM 17938.

In an embodiment of these aspects, the agent is a conditioned medium from a bacterial strain, preferably from a Lactic Acid bacterial strain and more preferably from a *Lactobacillus reuteri* strain, such as a conditioned medium from a bacterial strain capable of reducing spontaneous and/or induced TRPV1 activation, preferably from a Lactic Acid bacterial strain capable of reducing spontaneous and/or induced TRPV1 activation and more preferably from a *Lactobacillus reuteri* strain capable of reducing spontaneous and/or induced TRPV1 activation.

In an embodiment, the agent is a conditioned medium from Lactic Acid bacterial strains, preferably from *Lactobacillus reuteri* DSM 17938 or a *Lactobacillus reuteri* strain other than *Lactobacillus reuteri* DSM 17938. The medium used for such conditioned medium may be any medium appropriate for culturing Lactic Acid bacterial strains known in the art. In an embodiment, MRS (de Man, Rogosa & Sharpe) medium is used as starting material for producing conditioned medium from Lactic Acid bacterial strains, preferably from *Lactobacillus reuteri* DSM 17938. In an embodiment of the invention, conditioned medium from Lactic Acid bacterial strains, preferably from *Lactobacillus reuteri* DSM 17938, is freeze-dried before being introduced in or used as a composition.

In another embodiment, one or several components of conditioned medium from Lactic Acid bacterial strains, preferably from *Lactobacillus reuteri* DSM 17938, are isolated and administered as purified and/or enriched components to a subject in the form of a suitable composition. Examples of such components include proteins, peptides, enzymes and other molecules preferably secreted from the Lactic Acid bacterial strain into the medium. Also such components extracted directly from the Lactic Acid bacterial strains can be used according to the embodiments.

An appropriate mode of administration and formulation of the agent or composition, is chosen depending on the site of disease. A preferred mode of administration is oral, however, equally for some treatments intravenous or intramuscular injection will be appropriate.

Appropriate doses of the agent or composition can readily be chosen or determined by a skilled person depending on the disorder to be treated, the mode of administration and the formulation concerned.

In one embodiment, the TRPV1 receptor is modulated locally, e.g. by using perorally administered Lactic Acid bacteria that can modulate TRPV1 activation selectively in the GI tract, in a subject suffering from gastrointestinal pain and thereby minimizing any adverse effects in said subject. It is believed that this preferred administration route of the agent, in particular a Lactic Acid Bacterial strain selected by the method of the embodiments, will mainly affect TRPV1 activation locally, i.e. within the gastrointestinal system. Thus, agent will then have a beneficial effect in preventing or reducing gastrointestinal pain while minimizing any undesired TRPV1 modulation outside of the gastrointestinal system.

In the methods and uses of the present embodiments described herein, the terms "increase", "decrease", "reduce", etc., refer to a measurable change in levels, preferably a significant change in levels, more preferably a statistically significant change, preferably with a probability value of ≤0.05.

Preferred subjects are mammals, more preferably humans.

Where the intestinal motility disorder associated with gastrointestinal pain to be treated is constipation then preferred subjects are elderly patients or pregnant women. An elderly patient will generally be understood to be a patient aged 70 or over.

Where the intestinal motility disorder associated with gastrointestinal pain to be treated is colic, preferably this is infantile colic.

The uses of the agents, preferably Lactic Acid bacterial strains, selected according to the method of the embodiments include the reduction, prevention or alleviation of the relevant disorder or symptoms of disorder (e.g. can result in the modulation of disease symptoms). Such reduction, prevention or alleviation of a disorder or symptoms thereof can be measured by any appropriate assay.

It is an objective of an embodiment to find agents, such as Lactic Acid Bacteria, including parts or metabolites thereof, such as present in or extracted from a conditioned medium, suitable for treatment, reduction, prevention or modulation of gastrointestinal pain in e.g. specific motility disorders and/or other gastrointestinal pain disorders/diseases, by using the model herein based on the effect of the agent on spontaneous and/or induced TRPV1 activity.

In an embodiment the objective is to select a probiotic bacterial strain, such as Lactic Acid bacterial strain, which can be effective in preventing or reducing gastrointestinal pain associated with constipation in humans, especially elderly subjects or pregnant women.

In an embodiment, the objective is to select an agent, for example a Lactic Acid bacterial strain, that can be effective in preventing or reducing gastrointestinal pain associated with infantile colic.

In an embodiment the objective is to select an agent, for example a Lactic Acid Bacterial strain, that can be effective in treating, preventing or reducing gastrointestinal pain symptoms of Irritable bowel syndrome (IBS).

The following are some examples of the embodiments, which are not meant to be limiting of the use of the embodiments herein but to show practical examples in detail how the invention may be used. Example 1 relates to a mesenteric nerve bundle experiment showing that DSM 17938 inhibits mesenteric nerve firing frequency. Example 2 shows that DSM 17938 blocks capsaicin-induced calcium influx in DRG primary cultures. Example 3 demonstrates that DSM 17938 inhibits heart rate slowing evoked by gastric distention.

DEPOSIT INFORMATION

A deposit of the proprietary bacterial strain *Lactobacillus reuteri* DSM 17938 has been made with the Leibniz Institute DSMZ (DSMZ)—German Collection of Microorganisms and Cell Cultures, Inhoffenstr. 7B, D-38124 Braunschweig, Germany. The date of deposit for *Lactobacillus reuteri* DSM 17938 was Jan. 30, 2006. Upon issuance of a patent, all restrictions upon the deposits will be removed, and the deposits are intended to meet all of the requirements of 37 C.F.R. § 1.801-1.809. The DSMZ has issued accession number DSM 17938 for *Lactobacillus Lactobacillus reuteri* DSM 17938. These deposits will be maintained in the depository for a period of 30 years, or 5 years after the last request, or for the effective life of the patent, whichever is longer, and will be replaced as necessary during that period. Applicants do not waive any infringement of their rights granted under this patent or under the Plant Variety Protection Act (7 U.S.C. 2321 et seq.).

EXAMPLES

Example 1

Mesenteric Nerve Bundle Experiments
Extracellular Recordings

Adult male Swiss Webster mice (20-30 g) were procured from Charles River Laboratories (Wilmington, Mass.). The mice were killed by cervical dislocation. All ensuing procedures were ex vivo.

Segments of distal jejunum (~2.5 cm) with attached mesenteric tissue were removed from freshly killed animals and placed in a Sylgard-coated Petri dish filled with Krebs buffer (in mM): 118 NaCl, 4.8 KCl, 25 NaHCO$_3$, 1.0 NaH$_2$PO$_4$, 1.2 MgSO$_4$, 11.1 glucose, and 2.5 CaCl$_2$ bubbled with carbogen (95% O$_2$—5% CO$_2$). The oral and anal ends of each segment were cannulated with plastic tubing and emptied. The tissue was pinned to the Sylgard, and the mesenteric nerve bundle exposed. The Petri dish was placed onto the stage of an inverted microscope and the lumen gravity perfused at 0.5-1 ml/min with oxygenated Krebs or Krebs with additives (Perez-Burgos A., Wang B et al., American journal of physiology Gastrointestinal and liver physiology 2013; 304:G211-20). The serosal compartment was separately perfused with prewarmed (34° C.) Krebs at 3-5 ml/min. The nerve bundle was gently sucked into a glass pipette attached to a patch-clamp electrode holder (CV-7B; Molecular Devices, Sunnyvale, Calif.), and extracellular nerve recordings made using a Multi-Clamp 700B amplifier and Digidata 1440A signal converter (Molecular Devices). Electrical signals were bandpass-filtered at 0.1-2 kHz, sampled at 20 kHz, and stored on a personal computer running pClamp 10 software (Molecular Devices). Repeated distensions of segments were made by raising intraluminal pressure above 2 hPa. A constant gravity pressure head of 48 hPa was applied to the Krebs perfusing the lumen and pressure raised by closing the outflow tube for 1 min to a maximum of 3 consecutive distensions. Segments were allowed to rest for 9 min between distensions. Constitutive multiunit electrical activity was recorded in the absence of positive intraluminal pressure.

Vagotomy

Subdiaphragmatic vagotomy was carried out as previously described (van der Kleij H, O'Mahony C et al. American journal of physiology Regulatory, integrative and comparative physiology 2008; 295:R1131-7). Animals were allowed to recover for 10-14 days before harvesting the jejunum and mesenteric tissue for electrophysiological experiments. Sham vagotomies were performed in 3 animals. Postoperatively, the body weight and general health of the mice were measured daily. We found no evidence of significant differences in weight gain 1 week postsurgery in either vagotomized or sham-treated animals (data not shown). All vagotomized mice were tested for completeness of the procedure by recording after each experiment the responses to serosal application of cholecystokinin (CCK). Vagotomy was only deemed to have been effective when CCK did not increase mesenteric nerve firing rate (Perez-Burgos A., Wang B et al., American journal of physiology Gastrointestinal and liver physiology 2013; 304:G211-20).

Drugs and Bacteria

DSM 17938 were donated by BioGaia AB (Stockholm, Sweden), whereas *Lactobacillus rhamnosus* JB-1 were taken from a stock at the Brian-Body Institute at McMaster University (Ontario, Canada). All procedures were as reported previously (Kunze W A, Mao Y K et al., Journal of cellular and molecular medicine 2009; 13:2261-70, Ma X, Mao Y K et al., American journal of physiology Gastrointestinal and liver physiology 2009; 296:G868-75, Wang B, Mao Y K, FASEB journal: official publication of the Federation of American Societies for Experimental Biology 2010; 24:4078-88). Bacterial numbers were determined optically, and viability checked after plating on growth medium agar plates. Bacteria from frozen stocks were thawed, centrifuged at 2000 rpm for 15 min, and the pellet suspended in Krebs and again centrifuged and resuspended. Prior to use, bacteria were diluted to working concentrations with Krebs. Cholecystokinin (25-33) sulfated (CCK) was obtained from AnaSpec (Fremont, Calif.); nicardipine, capsaicin and 6-Iodonordihydrocapsaicin from Sigma-Aldrich, and ω-conotoxin GVIA (ω-Cg-GVIA) and ω-conotoxin MVIIC (ω-Cg-MVIIC) from Alomone Labs (Jerusalem, Israel). 6-Iodonordihydrocapsaicin and CCK were dissolved in DMSO; capsaicin was dissolved in ethanol to make stock solution aliquots. On the day of the experiment the aliquots were diluted in Krebs to working concentrations with final DMSO and ethanol concentrations of ≤0.01% and ≤0.1%, respectively.

Off-Line Data Analysis

Multi- and single-unit spontaneous firing frequencies were measured using Clampfit 10.2 (Molecular Devices) and Origin 8.5 (Northampton, Mass.) software. Multi- and single-unit spike recordings were routinely used to determine changes in the mesenteric nerve fiber firing rates induced by exposing the gut to differing stimuli or pharmacological agents (Perez-Burgos A., Wang B et al., American journal of physiology Gastrointestinal and liver physiology 2013; 304:G211-20). The timing of spikes in the multi-unit recording was determined using the peak detection module of Clampfit, and average firing frequency was calculated from interspike intervals. Single-units were extracted from the multiunit signal by spike shape matching using the spike shape template detection tool of Clampfit (computerized waveform analysis). After running the template detection algorithm, single-unit spike discrimination was always checked by visual inspection, and nonmatching spike events were discarded (<0.2%) (Perez-Burgos A., Wang B et al., American journal of physiology Gastrointestinal and liver physiology 2013; 304:G211-20).

Statistics

Data are expressed as means±SE with N referring to the total number of the jejunal segments recorded from, and n referring to the number of single fibers activity extracted from multi-unit recordings. We extracted a maximum of 6 single-units from each multi-unit recording. The Wilcoxon or unpaired t tests were used for paired or unpaired data comparisons, respectively; one-way and two-way ANOVA with Bonferroni's post hoc test were used to compare multiple groups as appropriate. Because large variations in spontaneous activity may occur between one preparation and another in multi-unit neural activity comparisons were paired with before and after treatment recordings made where each nerve bundle served as its own control to assure significant changes in each treatment or drug dose. The percentage of increase in firing above baseline frequency vs. capsaicin concentration (in the presence or absence of bacteria) was plotted and this fitted by a logistic dose-response equation [$Y=Bottom+(Top-Bottom/1+10^{LogEC50-X})$]. The parameters describing the logistic fits were compared using an extra sum-of-squares F test. All statistical tests were performed using Prism software 5.0 (GraphPad software, San Diego, Calif.).

Effects of DSM 17938 on Mesenteric Nerve Spontaneous Firing Frequency

Figure 1A:
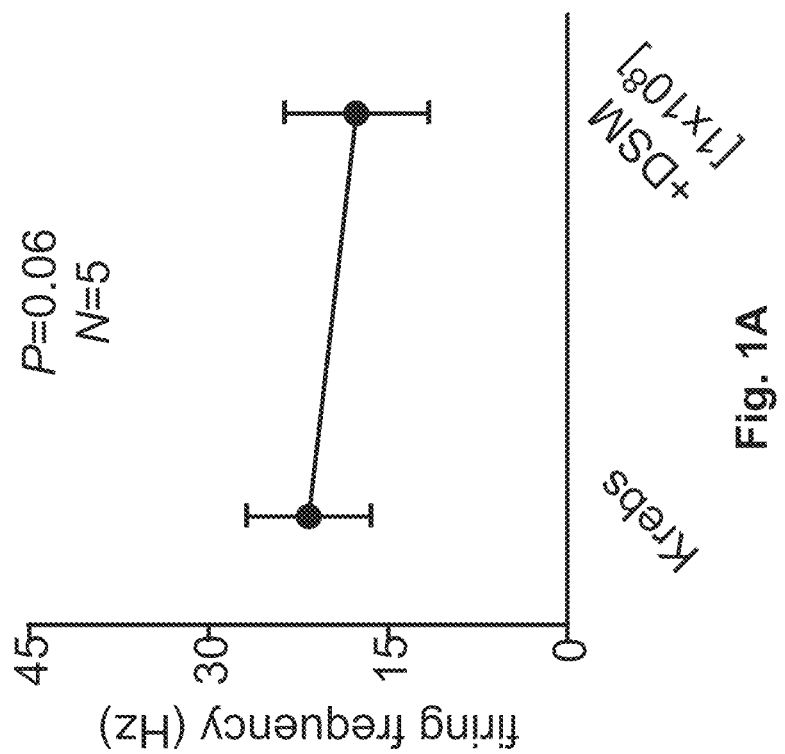
Figure 1E:
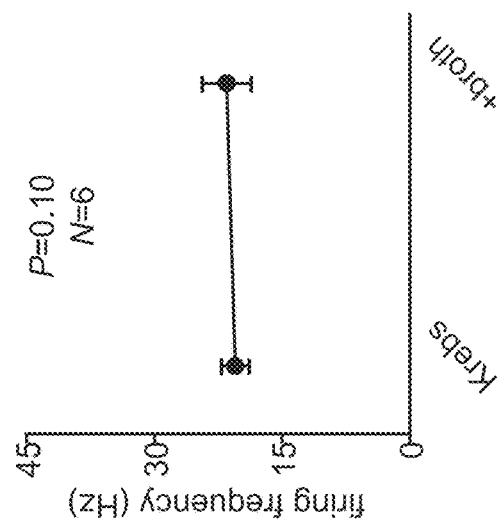
Figure 1D:
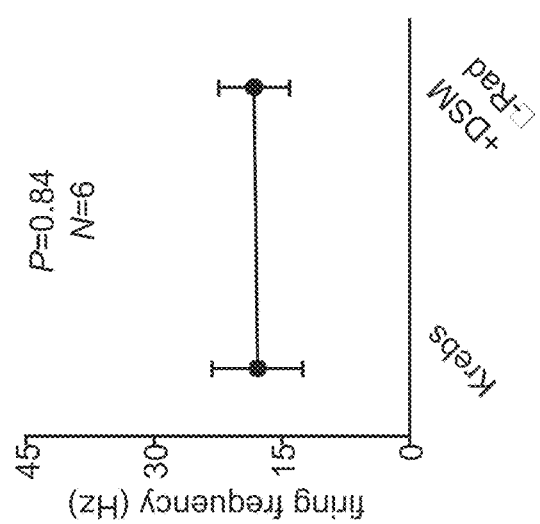
Figure 1C:
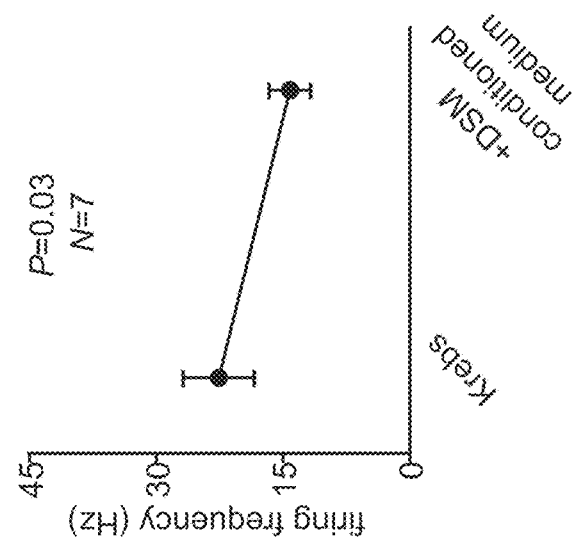

Luminal DSM 17938 influenced spontaneous multi-unit discharge of the mesenteric nerve (Perez-Burgos A., Wang B et al., American journal of physiology Gastrointestinal and liver physiology 2013; 304:G211-20). $1\times10^9$ cfu/ml intraluminal DSM 17938 caused a decrease in spontaneous multi-unit firing frequency by 22% from to 36.3±8.4 to 28.2±7.2 Hz (N=7, P=0.02, FIG. 1A); DSM 17938 at $1\times10^8$ cfu/ml changed the spontaneous discharge by 19% from 21.6±5.1 to 17.6±6 Hz, N=6, P=0.09, FIG. 1B). DSM 17938 conditioned medium (1:5) also decreased the spontaneous discharge by 37% from 22.6±4.2 to 14.17±2.4 Hz (N=7, P=0.03, FIG. 1C). However, γ-irradiated killed DSM 17938 or broth alone did not decrease afferent excitability: from 17.84±5.3 to 18.25±4.1 Hz (N=6, P=0.84), and from 20.48±1.6 to 21.49±2.8 Hz (N=6, P=0.10) respectively (FIGS. 1D-E).

Figures 2A, 2B:
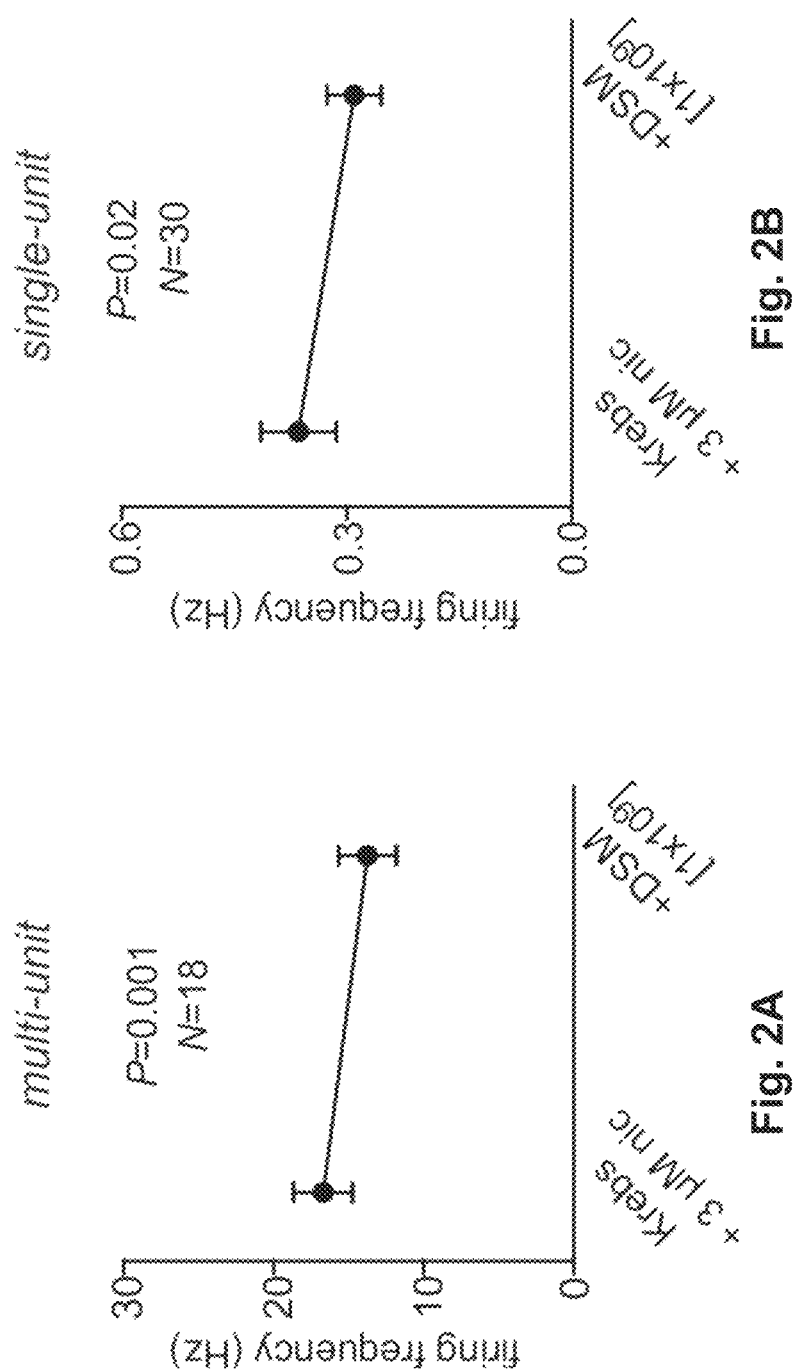
FIGS. 2A-2C show effects of DSM 17938 on spontaneous firing rate of spinal afferents. A) Multi-unit firing rate decreased when $1\times10^9$ cfu/ml DSM 17938 were added to the lumen (Wilcoxon test). B) Left panel, spinal single-unit firing was reduced by DSM 17938 (Wilcoxon test). C) Upper panels, representative traces of spontaneous multiunit discharge before and after adding DSM 17938; lower panels, superimposed waveforms of one single unit that occurred at times marked by "o" in upper traces.
Figure 2C:
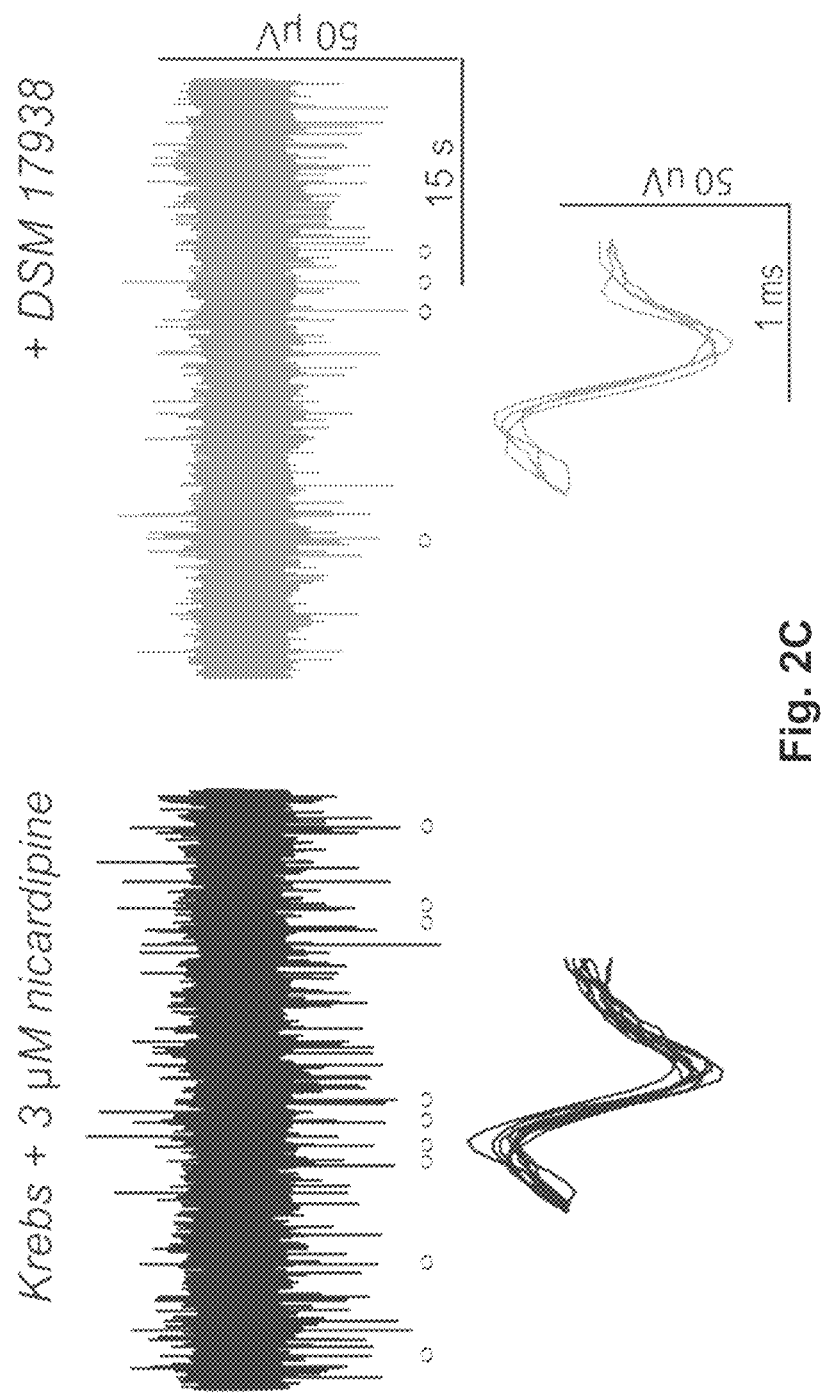

Vagotomy and Muscular Paralysis Did not Inhibit the Reduction by DSM 17938 of Mesenteric Nerve Spontaneous Firing We investigated whether the effect of DSM 17938 $1\times10^9$ cfu/ml on the spontaneous discharge was abrogated by prior vagotomy. To control possible direct actions of DSM 17938 on smooth muscle cells, we added here and in all subsequent experiments of spontaneous firing the L-type $Ca^{2+}$ channel blocker nicardipine (3 μM) which inhibits muscle contractions. Thus, after vagotomy and adding nicardipine, DSM 17938 reduced multi-unit firing frequency by 18% from 16.72±1.9 to 13.77±1.9 Hz (N=17, P=0.001, FIGS. 2A, 2C). The data from vagotomized animals and paralyzed muscle were then analyzed with respect to single-unit firing rates. DSM 17938 reduced single-unit firing frequency by 19% from 0.36±0.05 to 0.29±0.03 Hz (n=30, P=0.02, FIGS. 2B, 2C); of these fibers, the majority (20/30) showed a decrease in frequency of 36% from 0.42±0.06 to 0.27±0.04 Hz (P<0.0001), but the smaller fraction of remaining fibers increased their firing rate by 29% from 0.24±0.04 to 0.31±0.06 Hz (n=10/30, P=0.006).

DSM 17938 Diminished the Spinal Single-Unit Firing Frequency and the Response to Capsaicin by Insurmountable Partial Antagonism of TRPV1 Receptors We tested whether DSM 17938 could modify the capsaicin-induced firing frequency increase on single-unit excitation in tissue taken from previously vagotomized mice.

Figures 3A, 3B:
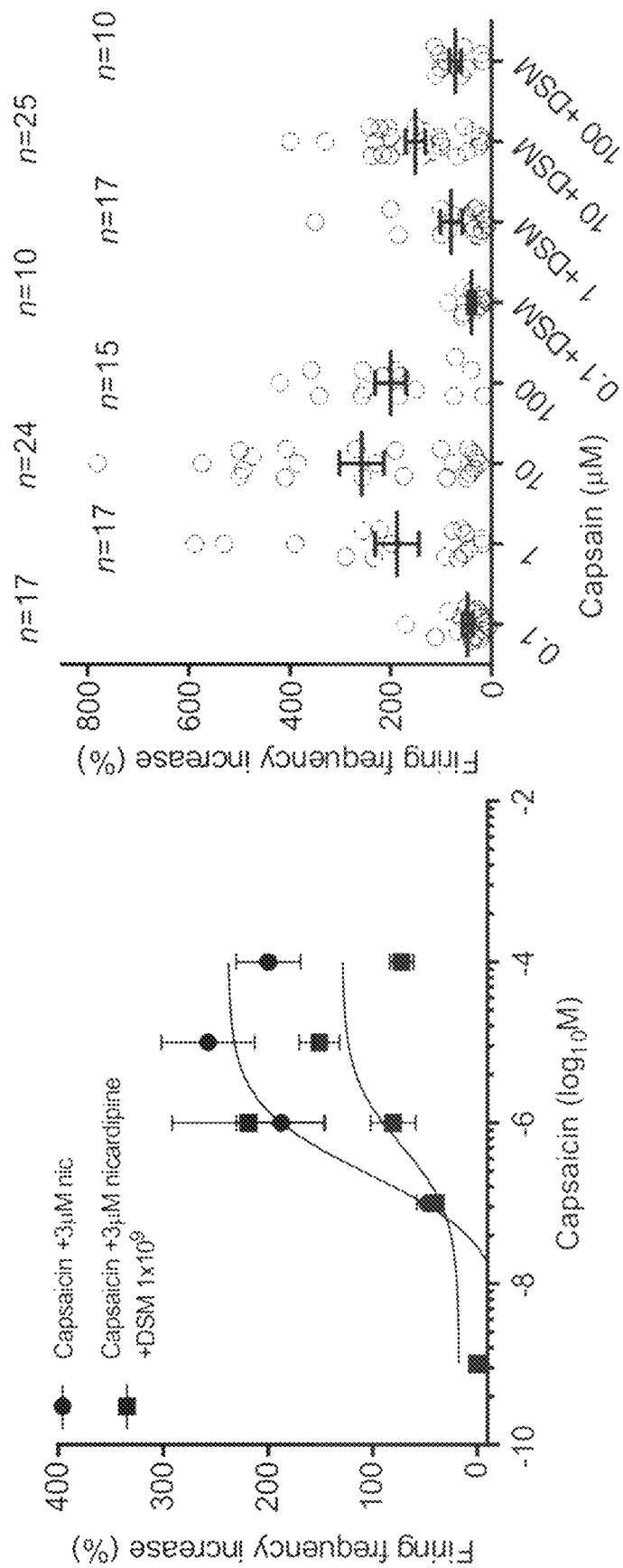
FIGS. 3A-3B show that DSM 17938 antagonized the excitatory response of spinal fibers by adding capsaicin to the serosal superfusate. A) Capsaicin dose-response curve from 113 spinal individual single units was plotted (●) and fitted with a three-parameter logistic equation, $EC_{50}=200$ nM. Max=238±27%; with additional 116 fibers a dose-response curve for capsaicin in the presence of $1\times10^9$ cfu/ml DSM 17938 was additionally plotted (■) and fitted with the same logistic equation, for which $EC_{50}=500$ nM and Max=129±17% (P=0.7 and P=0.004 for differences in $EC_{50}$ and Max respectively, extra sum-of-squares F test). B) Summary scatter plots with means and SEMs showing how single unit responses varied with increasing doses of capsaicin in the absence or presence of $1\times10^9$ cfu/ml DSM. (n) denotes the proportion of single units for each group.

Capsaicin applied to the serosal compartment increased the spontaneous multi- and single-unit firing rate, with onset latencies of ~60 s and in a dose-dependent manner. Given that the TRPV1 capsaicin sensitive receptors desensitize, and subsequent applications of the agonist may give rise to a diminished effect, we examined responses to a range of capsaicin doses (100 nM-100 µM) in individual jejunal segments. We did this with and without 20 min of prior intraluminal application of DSM 17938 $1\times10^9$ cfu/ml (N=25 for each curve, 5 segments per each concentration; ~6 spinal single-units were analyzed for each segment). The percentage of increase in firing frequency versus capsaicin concentration or capsaicin plus DSM 17938 concentration were plotted and fitted with a three-parameter logistic equation of the form $Y=Bottom+(Top-Bottom)/(1+10^{LogEC50-X})$. EC50 for capsaicin alone was 200 nM compared to 500 nM for capsaicin in the presence of DSM 17938 (P=0.71). The maximal response (Top) obtained with capsaicin was 238.4±27.5% vs. 129±17% obtained with capsaicin plus DSM 17938 (P=0.004, FIG. 3A). In agreement with previous reports, some spinal fibers were not excited by capsaicin. We examined if capsaicin excited spinal fibers directly, or whether the excitation depended on intramural synaptic transmission from enteric neurons to intraganglionic spinal endings. We added 1 µM capsaicin on the serosal compartment after intramural synaptic transmission was blocked by adding 500 nM each of the $Ca^{2+}$ blockers ω-Cg-GVIA and ω-Cg-MVIIC. Intramural synaptic blockage did not diminish the capsaicin-evoked excitation which was 187.5±42.9% (n=17) in the absence of the conotoxins and 219.1±72.6 (n=12) in their presence (P=0.947, FIG. 3B). We concluded that DSM 17938 action on spinal afferents does not involve intramural synaptic transmission.

Figure 7:
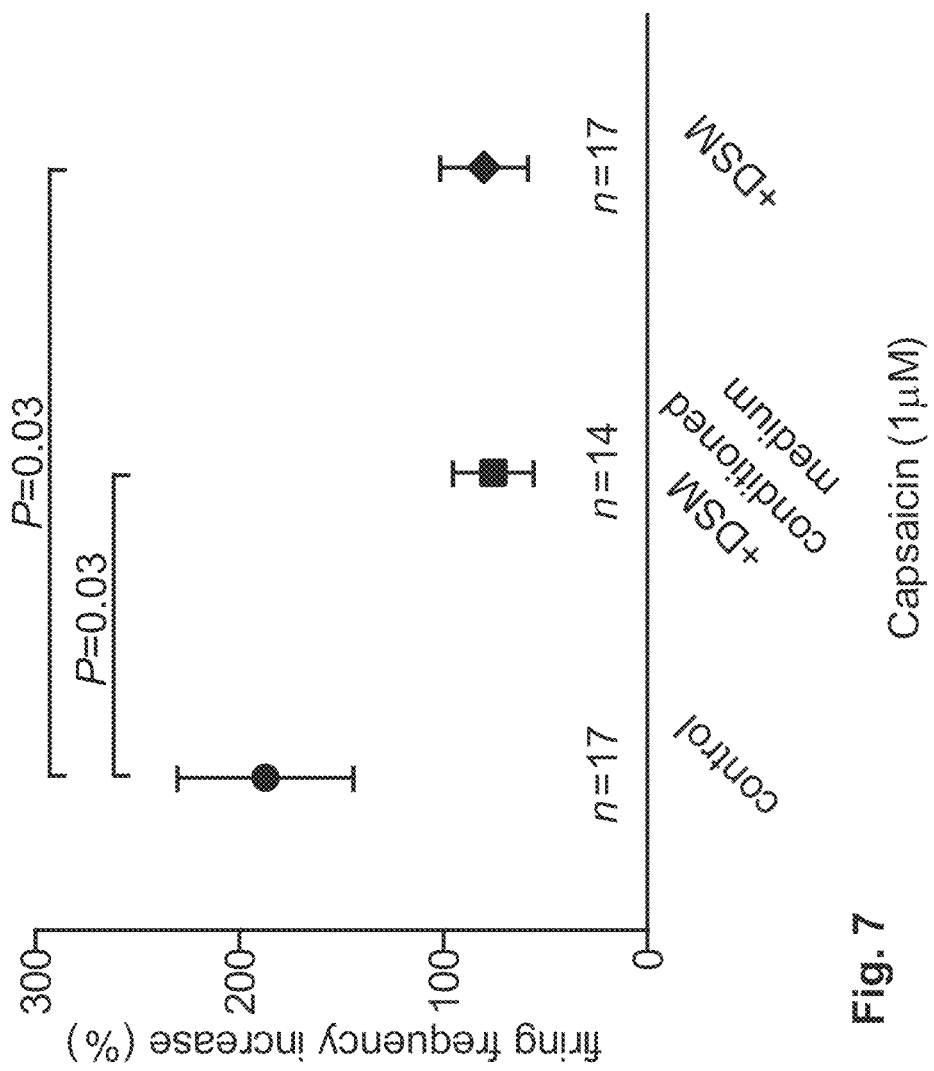
FIG. 7 shows that the DSM 17938 induced decrease of the capsaicin excitatory actions on spinal afferents was mimicked by DSM 17938 conditioned medium. Summary plot showing the firing frequency increase of single-unit spinal fibers induced by 1 μM capsaicin in control conditions, with DSM 17938 conditioned medium (1:5) or with $1\times10^9$ cfu/ml DSM 17938 (P=0.02, one-way ANOVA test; post-hoc P values, Holm-Sidak's multiple comparisons test).

Effects of DSM 17938 Conditioned Medium Containing DSM 17938 Bacterial Released Products Reduced Capsaicin Actions on Spinal Fibers We tested whether the DSM 17938 bacterial products underlie TRPV1 antagonism on mesenteric afferents. The DSM 17938 target in the mesenteric afferents are predominantly spinal fibers, given that the percentage of DSM 17938-induced reduction of spontaneous firing frequency was very similar with and without previous vagotomy (18% vs. 22% respectively); then, we applied 1 µM capsaicin in non-vagotomized mesenteric fibers which received a previous intraluminal application of DSM 17938 conditioned medium for 20 min. DSM 17938 conditioned medium (1:5) inhibited the capsaicin-induced firing frequency increase (%) on mesenteric single fibers from 187.5±43% (control group, N=17) to 74.89±22% (N=14), and was similar to the percentage of increase induced by capsaicin on spinal fibers with $1\times10^9$ cfu/ml DSM 17938 treatment (80.29±22%, N=17) (P=0.02, one-way ANOVA test; FIG. 7).

DSM 17938 or TRPV1 Antagonism Reduced Distension-Evoked Firing

Figure 4B:
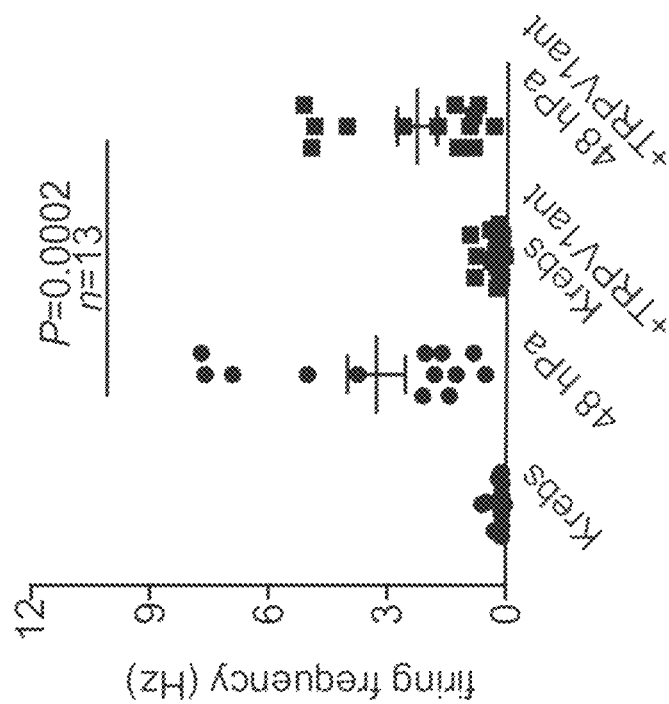
FIGS. 4A-4B show that DSM 17938 or a TRPV1 antagonist reduce distension-evoked excitatory response in spinal single units. A) Scatter graphs showing that adding $1\times10^9$ DSM 17938 to the lumen reduced the increase in spinal single unit firing rate evoked by raising intraluminal pressure to 48 hPa. B) Adding 10 μM of the TRPV1 antagonist 6-Iodonordihydrocapsaicin to the lumen mimicked the effect of adding DSM 17938 (Wilcoxon tests).
Figure 4A:
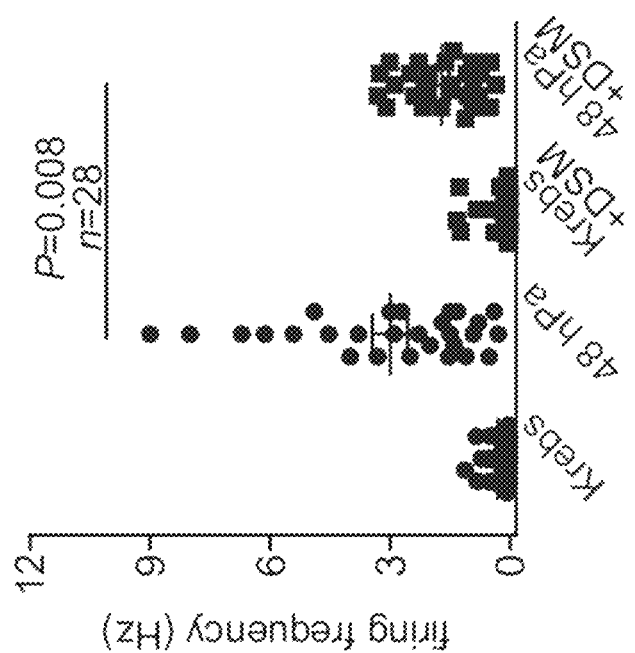

In the absence of nicardipine to allow muscle contraction, we recorded multi- and single-unit firing frequency of fibers presumed to be nociceptors (Grundy D, Gut 2004; 53 Suppl 2:ii5-8). We tested whether DSM 17938 could reduce their excitatory response evoked by raising intraluminal pressure to a nociceptive intensity of 48 hPa (36 mmHg) (Perez-Burgos A., Wang B et al., American journal of physiology Gastrointestinal and liver physiology 2013; 304:G211-20). The first response of these fibers to gut distension is generally higher than that obtained with a subsequent distension, but remains constant for up to 3 further distensions (Perez-Burgos A., Wang B et al., American journal of physiology Gastrointestinal and liver physiology 2013; 304:G211-20). We thus used the $2^{nd}$ of 3 successive distensions for comparisons. Multi-unit firing was 111.5±16.7 Hz during distension, but after adding DSM 17938 for 20 min, distension increased firing to only 86.5±10.6 Hz (N=5, P=0.31). Spinal single-unit firing frequency was 3.01±0.44 Hz during distension, but in the presence of DSM 17938 firing was 1.71±0.16 during distension (n=28, P=0.008, FIG. 4A). The pre-distension firing frequency was 0.31±0.05 vs. 0.25±0.07 Hz (n=28, P=0.053, FIG. 4A) for control vs. added DSM 17938. The TRPV1 antagonist 6-Iodonordihydrocapsaicin (10 µM) mimicked the effect of DSM 17938 on the single-unit response by decreasing the response to distension from 3.26±0.73 to 2.23±0.50 Hz (n=13, P=0.0002, Wilcoxon test, FIG. 4B in the absence of nicardipine).

Example 2

DSM 17938 Blocked the $Ca^{2+}$ Rise Induced by Capsaicin in DRG Neuronal Primary Cultures Dorsal Root Ganglion (DRG) Primary Cultures The spinal column was removed from the body, transferred to a beaker containing ice-cold Krebs, and bisected longitudinally. DRG were exposed and collected from the thoracolumbar levels. Whole DRG were washed twice with sterile Leibovitz's L-15 medium (GIBCO, Gaithersburg, Md.), and incubated for 40 min in collagenase type 1 at 1 mg/ml (Sigma-Aldrich; Oakville, ON, Canada) and 0.5 ml trypsin (0.25%, GIBCO) in 20 ml L-15 at 37° C. After further addition of 5 ml L-15 containing 10% fetal bovine serum (FBS, GIBCO), the ganglia were centrifuged for 5 min at 1,000 rpm, then washed twice with growth medium (L-15, containing 10% FBS, 1% Penicillin/Streptomycin/Glutamine, 1% HEPES and 1% Na Pyruvate). The DRG were placed in 2 ml of growth medium and triturated 10 times. The ganglia were then centrifuged for 10 s at 500 rpm and the supernatant transferred to a sterile tube. They were resuspended in 2 ml of growth medium, triturated repeatedly until the volume of supernatant transferred was 10 ml, centrifuged for 5 min at 1,000 rpm, and the final pellet resuspended in 3 ml of growth medium. Neurons were plated onto 3 glass bottomed Petri dishes coated with poly-d-lysine (MatTek, Ashland, Mass.). An additional 1.5 ml of growth medium was added to each dish after 30 min and the whole incubated for 24 h at 37° C. with carbogen.

$Ca^{2+}$ Imaging

DRG neurons were placed within a plexiglass recording dish and loaded with the $Ca^{2+}$ indicator Fluo-4-AM (8 µM) diluted in Krebs with 0.1% pluronic acid (in DMSO) at 37° C. for 60 min. The dish was placed into the recording compartment and superfused with fresh Krebs (~34° C.) for 15 min to allow dye wash out. Cells were observed on an inverted microscope (Nikon eclipse TE 2000-S, Melville, N.Y.) and imaged using a Rolera-XR camera (Surrey, BC, Canada). Fluorescence intensity in individual neurons was recorded by Simple PCI 6 software (Compix Inc, Imaging systems, Sewickley, Pa.). Drugs were delivered via a micropipette attached to an electronically controlled pressure pulse puffer (Picospritzer II; General Valve, Fairfield, N.J.) with the tip <100 µm from the cell. Images, recorded at 0.9 frame/s, were stored on a local hard drive. Image files were analyzed off-line using Image J software (NIH, USA, http://imagej.nih.gov/ij). The increase in Fluo-4 $Ca^{2+}$ when applying capsaicin was measured as the ratio ($F/F_0$) fluorescence intensity after capsaicin (F) divided by the intensity before capsaicin ($F_0$). Bacteria and drugs were handled as in Example 1.

Results

Figures 5A, 5B:
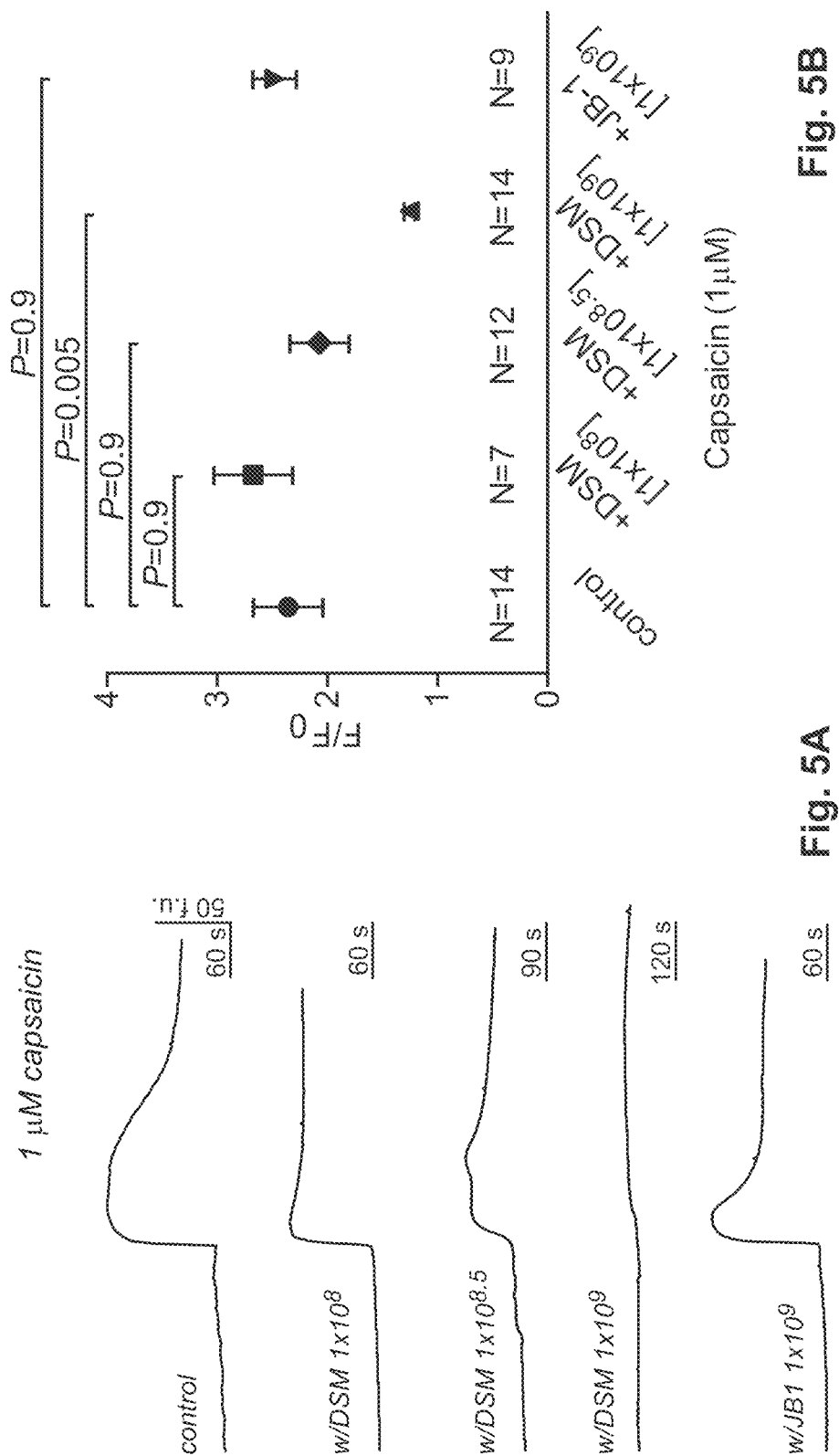
FIGS. 5A-5B show that DSM 17938 reduced capsaicin-evoked $Ca^{2+}$ rise in dorsal root ganglia neuron somata. A) 1 μM capsaicin evoked an increase in DRG neurons $Ca^{2+}$ entrance that was dose-dependently diminished by intraluminal DSM 17938 and unaffected by $1\times10^9$ cfu/ml JB-1. B) Summary plot showing how the ratio ($F/F_0$) of maximal $Ca^{2+}$ fluorescence (F) evoked by capsaicin to baseline $Ca^{2+}$ fluorescence ($F_0$) varied with DSM 17938 concentration or JB-1. (P values, Bonferroni's multiple comparisons test).

The specificity of the effect of DSM 17938 on spinal neurons was further investigated by testing the bacteria's ability to inhibit the response of the TRPV1 receptor agonist capsaicin. In these experiments, JB-1 was also included. JB-1 (*Lactobacillus rhamnosus*) has previously been shown to reduce pain and firing discharge of DRG single fibers induced by gastric distension (Duncker et al., The Journal of Nutrition 2011). Since the opening of TRPV1 channels raises the intracellular $Ca^{2+}$ concentration we used $Ca^{2+}$ imaging of DRG neuronal primary culture for these experiments. Puffing 1 µM capsaicin onto DRG neurons evoked an increase in intracellular $Ca^{2+}$ within ~30 s (FIG. 5A). Since the TRPV1 channel may desensitize with repeated ligand exposure, we only applied capsaicin once to each culture dish. We then added either DSM 17938 or JB-1 30 min before applying capsaicin. DSM 17938 at $1 \times 10^9$ cfu/ml decreased the fluorescence rise ratio from 2.36±0.31 (control group, N=14) to 1.25±0.04 $F/F_0$. But, $1 \times 10^8$ cfu/ml DSM 17938 changed $F/F_0$ to 2.67±0.35 and $1 \times 10^{8.5}$ cfu/ml DSM 17938 to 2.07±0.27. Adding $1 \times 10^9$ cfu/ml of JB-1 had little effect and changed the F/F0 ratio to 2.48±0.19 (N=9), which is similar to the ratio obtained with capsaicin alone (FIG. 5B). These results demonstrate that DSM 17938 can block the $Ca^{2+}$ rise induced by capsaicin in DRG neuronal primary cultures.

Example 3

DSM 17938 Inhibited Heart Rate Slowing Evoked by Gastric Distension

A total of 17 rats were assigned to 2 groups. Upon arrival, rats were allowed to acclimatize for 1 week followed by handling for 1 week (10 min/d) to minimize stress effects during experiments. Rats were gavaged each morning for 9 d with either 0.2 ml ($1 \times 10^9$ cfu/ml) live DSM 17938 in Krebs or only Krebs as control (vehicle). The methods for GD have been previously published (Tougas, Wang, American Journal of Physiology 1999; 277:R272-8). In brief, rats were fasted overnight, anesthetized with a mixture of ketamine hydrochloride (75 mg/kg body weight) and xylazine (10 mg/kg body weight) intraperitoneally. Supplemental anesthesia was given as necessary. After a mid-line laparotomy, a distension device consisting of a ball-shaped gastric balloon (2-cm i.d.) affixed to a Teflon catheter (20 cm) was inserted into the stomach through a small incision in the proximal duodenum and connected to a barostat system (Distender, G&J Electronic, Toronto, Canada). The cardiac response was measured while inflating the balloon with air to pressures of 40 and 60 mm Hg for 60 s. Ten min of rest was allowed for recovery after every distension. Only one set of distensions was applied to each rat to avoid possible compensatory mechanisms and rats were killed after the measurements before gaining consciousness. Continuous recordings of heart rate were performed through a surface electrocardiogram consisting of 3 needle electrodes applied to the left and right shoulders and the right hind legs. The signal was amplified and recorded on a personal computer using a commercial data acquisition program (Experimenter's Workbench, DataWave Technologies, Loveland, Colo.). The heart rate was measured for 60 s before, during, and after each distension for a total of 180 s. Heart rate (HR) recording before each distension allowed correction for possible baseline changes due to variations in levels anesthesia and ensured any heart rate response could be linked to the distension. To control the effect of GD over time, the data are presented as mean change from resting HR (100%=rest) using the mean HR recorded for a period of 10 s during distension (10, 20, 30, 40, 50, and 60 s). Groups were compared using the mean of HR changes (percent of resting HR) in all rats of the same group during the 60 s of each distension (40 and 60 mm Hg). Bacteria and drugs were handled as in Example 1.

Results

The decrease in heart rate evoked by 40 mm Hg was not changed by gavaging DSM 17938 (P=0.121, FIG. 6A) (N=8 and 9 with vehicle and DSM 17938 respectively). Inflation with 60 mm Hg decreased heart rate within 10 s which persisted for 30 s during distension (FIG. 6B). Gavaging with DSM 17938 for 9 d prior to testing moderated the response to 60 mm Hg (P=0.028, unpaired t-test, FIGS. 6A, 6B). Gastric compliance (volume/pressure) did not differ between animals treated with vehicle or DSM 17938, for gastric distension pressures of 40 or 60 mm Hg (data not shown). These results demonstrate an antinociceptive effect by the bacteria.

The invention claimed is:

1. A method for selecting a lactic acid bacterial strain for reducing gastrointestinal pain locally in a subject, said method comprising:
    contacting a cell expressing transient receptor potential vanilloid 1 (TRPV1) with the bacterial strain;
    measuring spontaneous and/or induced TRPV1 activation in said cell following the contacting; and
    selecting said bacterial strain effective in reducing gastrointestinal pain locally when said measured spontaneous and/or induced TRPV1 activation is lower than control TRPV1 activation.

2. The method according to claim 1, wherein measuring said spontaneous and/or induced TRPV1 activation comprises measuring Ca2+ influx in said cell induced by capsaicin, pH change and/or heat.

3. The method according to claim 1, wherein measuring said spontaneous and/or induced TRPV1 activation comprises measuring temperature-gated ion-channel activity in said cell.

4. The method according to claim 3, wherein said bacterial strain is a *Lactobacillus reuteri* strain.

5. The method according to claim 4, wherein the *Lactobacillus reuteri* bacterial strain is *Lactobacillus reuteri* DSM 17938 having been deposited under DSMZ Accession No. DSM 17938.

6. The method according to claim 1, wherein said bacterial strain is a *Lactobacillus reuteri* strain.

7. The method according to claim 6, wherein the *Lactobacillus reuteri* bacterial strain is *Lactobacillus reuteri* DSM 17938 having been deposited under DSMZ Accession No. DSM 17938.

* * * * *